United States Patent [19]

Cullis et al.

[11] Patent Number: 5,008,050

[45] Date of Patent: Apr. 16, 1991

[54] EXTRUSION TECHNIQUE FOR PRODUCING UNILAMELLAR VESICLES

[75] Inventors: Pieter R. Cullis; Michael J. Hope; Marcel B. Bally, all of Vancouver, Canada

[73] Assignee: The Liposome Company, Inc., Princeton, N.J.

[21] Appl. No.: 310,495

[22] Filed: Feb. 13, 1989

Related U.S. Application Data

[60] Continuation of Ser. No. 788,017, Oct. 16, 1965, abandoned, which is a division of Ser. No. 622,690, Jun. 20, 1984, abandoned.

[51] Int. Cl.$^5$ .................... A61K 9/133; A61K 37/22
[52] U.S. Cl. .................... 264/4.3; 424/1.1; 424/450; 428/402.2; 436/829
[58] Field of Search .................... 264/4.3; 428/402.2; 424/450; 436/829

[56] References Cited

U.S. PATENT DOCUMENTS

| | | | |
|---|---|---|---|
| 4,016,100 | 4/1977 | Suzuki et al. | 264/4.3 |
| 4,078,052 | 3/1978 | Papahadjopoulos | 424/36 |
| 4,235,871 | 11/1980 | Papahadjopoulos et al. | 424/19 |
| 4,308,166 | 12/1981 | Marchetti et al. | 264/4.6 X |
| 4,529,561 | 7/1985 | Hunt et al. | 264/4.3 |
| 4,532,089 | 7/1985 | MacDonald | 264/4.3 |

OTHER PUBLICATIONS

Bosworth, Mark et al., "Liposome Dialysis for Improved Size Distribution," *Journal of Pharmaceutical Sciences*, vol. 71, No. 7, Jul. 1982, pp. 806–812.

Millipore 1978 Catalogue and Purchasing Guide, Cat. No. MC 177/V, Millipore Corp., Bedford, Mass., 12/1976, pp. 46–48, 70.

Porter, M. C. et al., "Membrane Ultrafiltration," Chem. Tech., Jan. 1971, pp. 56–63.

Abra, R. M. and Hunt, C. A., *Biochim. Biophys. Acta*, 666: 493–503 (1981).

Allen, et al., *Biochimica et Biophysica Acta*, 601: 328 (1980).

Barenholz, et al., *FEBS Lett.*, 99: 210 (1979).

Batzri, S. et al., *Biochimica et Biophysica Acta*, 298: 1015 (1973).

Blaurock, A. E., *Biochim. Biophys. Acta.*, 650: 167–207 (1982).

Bottcher, C. J. F., et al., *Anal. Chim. Acta*, 24: 203–204 (1961).

Comfurius, P. et al., *Biochim. Biophys. Acta*, 488: 36–42 (1977).

Deamer, *Annals New York Academy of Sciences*, 308: 250–258 (1978).

Dyer, J., *Methods of Biochemical Analysis*, P. Glick (Ed.), vol. 3, p. 111, Interscience (1956).

Fiske, C. H. and Subbarrow, Y., *J. Biol. Chem.*, 66: 375–379 (1925).

Hamilton, et al., *Journal of Lipid Research*, 21: 981 (1980).

Hope, M. J. and Cullis, P. R., *Biochem. Biophys. Res. Commun.*, 92: 846–852 (1980).

Ladbrooke, B. D. and Chapman, D., *Chem. Phys. Lipids*, 3: 304–367 (1969).

Miller, R. G., *Nature*, 287: 166 (1980).

Mimms, L. T., et al., *Biochemistry*, 20: 833–840 (1981).

Olson, et al., *Biochimica et Biophysica Acta*, 557: 9 (1979).

Ostro, Marc J., ed., *Liposomes*, Chapter 1, Marcel Dekker, Inc., New York, (1983).

(List continued on next page.)

*Primary Examiner*—Richard D. Lovering
*Attorney, Agent, or Firm*—Allen Bloom; Catherine Kurtz; Ronald G. Ort

[57] ABSTRACT

A method for reducing the lamellarity of a population of liposomes is provided which comprises repeatedly passing the liposomes under pressure through a filter which has a pore size equal to or less than about 100 nm. In certain embodiments, the method is used to convert a population of previously formed multilamellar liposomes into a population of substantially unilamellar liposomes. In accordance with other aspects of the disclosure, liposomes are prepared directly from a lipid powder or pellet and buffer without the use of any solvents, detergents or other extraneous materials.

29 Claims, 9 Drawing Sheets

OTHER PUBLICATIONS

Pick, U., *Archives of Biochemistry and Biophysics*, 212: 186–194 (1981).
Roe, J. H., *J. Bio. Chem.*, 212: 335–343 (1955).
Schieren, H., et al., *Biochim. Biophys. Acta*, 542: 137–153 (1978).
Schuh, J. R., et al., *Biochim. Biophys. Acta*, 687: 219–225 (1982).
Singleton, et al., *Journal of the American Oil Chemical Scoiety*, 42: 53 (1965).
Szoka, Jr., et al., *Proc. Natl. Acad. Sci. U.S.A.*, 75: 4194 (1978).
Szoka, F. and Papahadjopoulos, D., *Ann. Rev. Bioeng.*, 9: 467–508 (1980).
Szoka, et al., *Biochimica et Biophysica Acta*, 601: 559 (1980).
Tilcock, C. P. S. and Cullis, P. R., *Biochim. Biophys. Acta*, 641: 189–201 (1981).
van Dijck, P. W. M., et al., *Biochim. Biophys. Acta*, 506: 183–191 (1978).
van Venetie, et al., *J. Micros.*, 118: 401–408 (1980).
Barenholz, et al., *Biochemistry*, 16: 2806 (1977).
Brendzel, et al., *Biochimica et Biophysica Acta*, 596: 129 (1980).
Enoch et al., *Proc. Natl. Acad. Sci. U.S.A.*, 76: 145 (1979).
Huang, Ching-hsien, *Biochemistry*, 8: 344 (1969).
Koppel, D. E., *Journal of Chemical Physics*, 57: 4814 (1972).
Reeves et al., *J. Cell. Physiol.*, 73: 49 (1969).
Rhoden et al., *Biochemistry*, 18: 4173 (1979).
Schullery et al., *Chemistry and Physics of Lipids*, 12: 75 (1973).
Watts et al., *Biochemistry*, 17: 1792 (1978).
Chen et al., *J. of Biochem. and Biophys. Methods*, 1: 189–192 (1979).
Louni et al., International Meeting of French Physical Chemistry Society, 1982 (abstract only).
Morii et al., *Yakugaku Zasshi*, 101: 1023–1029 (1981) (abstract only).
Morii et al., *Int. J. of Pharmaceutics*, 17: 215–224 (1983).
Filtration: Nucleopore Filtration Products for the Laboratory, Catalog Lab 50, Nucleopore Corporation, circa 1980, pp. 72, 75.

FIG. 8 a
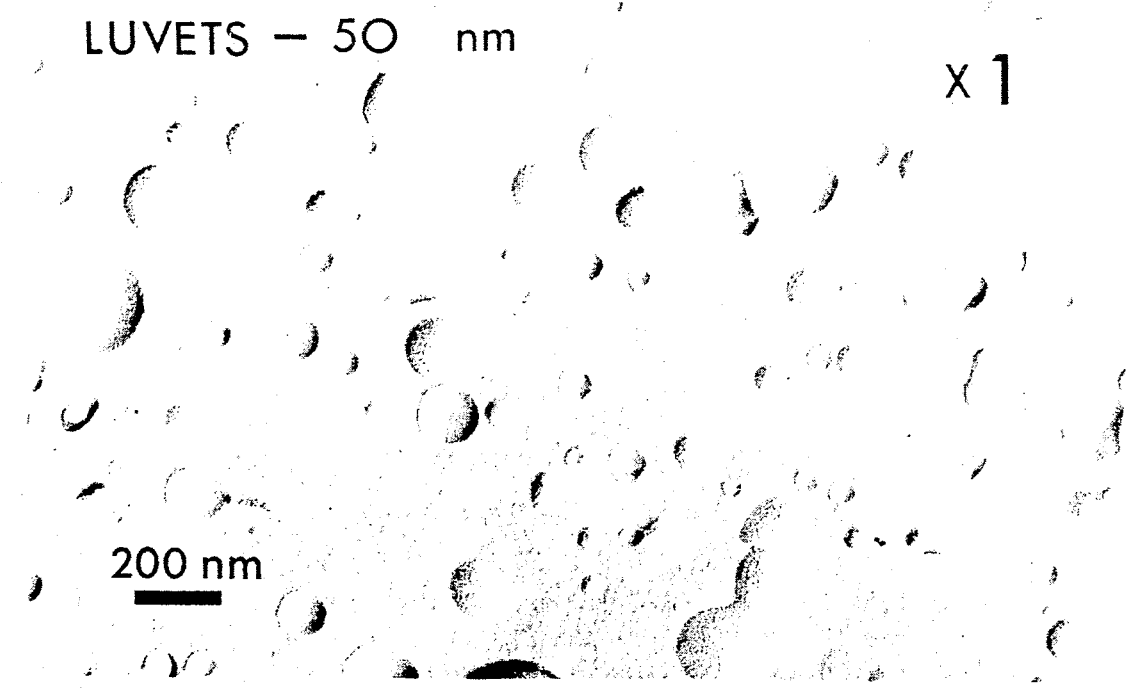
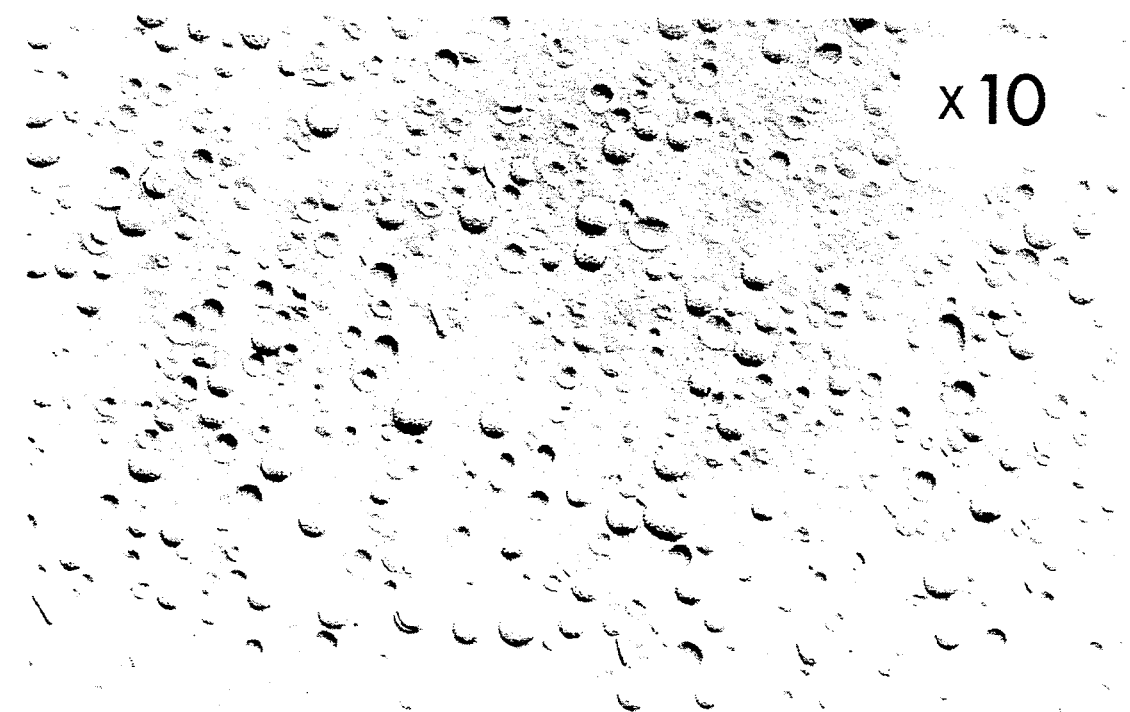
FIG. 8 b

EXTRUSION TECHNIQUE FOR PRODUCING UNILAMELLAR VESICLES

This application is a continuation of application Ser. No. 06/788,017, filed Oct. 16, 1985, now abandoned; which was a division of application Ser. No. 06/622,690, filed June 20, 1984, now abandoned.

BACKGROUND OF THE INVENTION

1. Field of the Invention

This invention relates to liposomes and in particular to an extrusion technique for the rapid production of unilamellar liposomes.

2. Description of the Prior Art

As is well known in the art, liposomes are closed vesicles having a lipid bilayer membrane surrounding an aqueous core. In general, liposomes of the following three types have been produced: (1) multilamellar vesicles (MLVs) wherein each vesicle includes multiple concentric bilayer membranes stacked one inside the other in an onion skin arrangement: (2) small unilamellar vesicles (SUVs) having only one bilayer membrane per vesicle and having diameters ranging up to about 50 nm; and (3) large unilamellar vesicles (LUVs), again having only one bilayer membrane per vesicle, but in this case having diameters greater than about 50 nm and typically on the order of 100 nm and above.

A review of these three types of liposomes, including methods for their preparation and various uses for the finished liposomes, can be found in the text *Liposomes*, Marc J. Ostro, ed., Marcel Dekker, Inc., New York, 1983, the pertinent portions of which are incorporated herein by reference. See also Szoka, Jr., et al., *Ann. Rev. Biophys. Bioeng.*, 9:467 (1980), the pertinent portions of which are also incorporated herein by reference.

Other types of liposomes which have been developed include stable plurilamellar vesicles (SPLVs), monophasic vesicles (MPVs), and steroidal liposomes. Descriptions of these vesicles and methods for preparing them can be found in copending and commonly assigned U.S. patent applications Ser. Nos. 476,496, 521,176, and 599,691, filed on Mar. 24, 1983, and now U.S. Pat. No. 4,522,803 Aug. 8, 1983, and now U.S. Pat. No. 4,588,578 and Apr. 12, 1984, and now abandoned respectively, the pertinent portions of which are incorporated herein by reference.

The present invention relates to an improved method for the production of liposomes. In particular, it relates to an improved method for producing unilamellar liposomes of both the large and small types.

Prior to the present invention, large unilamellar liposomes (LUVs) were commonly produced by one of the following three methods: (1) reverse-phase evaporation, (2) detergent dilution, and (3) infusion procedures using various solvents. See *Liposomes, supra*, Ch. 1, pages 37-44.

In the reverse-phase evaporation technique, an aqueous buffer is introduced into a mixture of phospholipid and an organic solvent to produce "inverted micelles," i.e., droplets of water stabilized in the organic solvent by being surrounded by a phospholipid monolayer. Evaporation of the solvent causes the micelles to coalesce and form the desired liposomes. See, for example, Szoka, Jr., et al., *Proc. Natl. Acad. Sci.* USA, 75:4194 (1978); and U.S. Pat. No. 4,235,871 to Papahadjopoulos et al.

In the detergent dilution approach, lipid, detergent and an aqueous solution are mixed together and sonicated to form the desired vesicles. Separation techniques, such as, gel filtration, are then used to remove the detergent and thus produce the finished liposomes.

In the infusion procedures, lipid is dissolved in a solvent, e.g., pentane or diethyl ether, and the lipid-solvent solution is infused into an aqueous solution under conditions that cause the solvent to vaporize and thus produce the desired liposomes. See, for example, Deamer, *Annals New York Academy of Sciences*, 308:250-258 (1978).

Other techniques which have been used to produce LUVs include fusion techniques whereby a population of SUVs is treated so as to cause individual SUVs to fuse with each other to form LUVs. For example, U.S. Pat. No. 4,078,052 to P. Demetrios Papahadjopoulos describes a technique wherein calcium ions are used to fuse SUVs into cochleate cylinders, and the cylinders are then treated with a calcium chelating agent such as EDTA to form the desired LUVs. Rapid freezing of SUVs, followed by slow thawing, has also been used to produce LUVs by fusion. See, for example, U. Pick, *Archives of Biochemistry and Biophysics*, 212:186 (1981).

With regard to the production of SUVs, as with LUVs, a variety of techniques have been employed in the past. See *Liposomes, supra*, Ch. 1, pages 33, 36. The earliest technique involved sonication to clarity of a suspension of lipid in an aqueous solution using a probe or bath sonication unit. Other techniques have included infusion procedures along the lines of those used for producing LUVs but with ethanol as the solvent (see S. Batzri and E. Korn, *Biochimica et Biophysica Acta*, 298:1015 (1973)), and a technique employing multiple passes of MLVs through a French press operated at a pressure of 20,000 psi (see, for example, Hamilton, Jr., et al., *Journal of Lipid Research*, 21:981 (1980); and Barenholz, et. al., *FEBS Lett.*, 99:210 (1979)).

In addition to the basic techniques used to produce liposomes, various ancillary techniques have been developed for post-preparation treatment of liposomes to improve their properties. In particular, many of the LUV techniques described above have required sizing of the finished liposomes by filtration using, for example, a series of polycarbonate filters. See *Liposomes, supra*, Ch. 1, pages 37-39, 45: and Szoka, et al., *Biochimica et Biophysica Acta*, 601:559 (1980). Series of polycarbonate filters have also been used to size MLVs. See F. Olson, et al., *Biochimica et Biophysica Acta*, 557:9 (1979), and Bosworth, et al., *Journal of Pharmaceutical Sciences*, 71:806 (1982).

Although each of the foregoing techniques can be used to produce liposomes, none of these techniques are totally satisfactory. For example, each of the commonly used LUV techniques involves combining the components making up the liposome with a lipid solubilizing agent, i.e., either an organic solvent or a detergent. As is well known in the art, solvents and detergents can adversely effect many materials, such as enzymes, which one may want to encapsulate in liposomes, and thus these techniques cannot be used with these materials. Also, in applications such as the generation of drug carrier systems, the possible presence of these potentially toxic agents is undesirable.

Moreover, these techniques often require lengthy dialysis procedures which can never completely remove the solvent or detergent employed. See, for example, T. Allen, et al., *Biochimica et Biophysica Acta*, 601:328 (1980). Further, a variety of protocols are required depending on the lipid species. For example, the limited solubility of certain lipids (e.g., cholesterol, phosphatidylethanolamine (PE), and phosphatidylserine (PS)) in ether or ethanol requires modification of techniques employing these solvents. Alternatively, detergent dialysis procedures employing non-ionic detergents such as octylglucoside are tedious to apply as they can involve several days of dialysis. Plainly, the need to separate lipid solubilizing agents from the finished liposomes materially decreases the usefulness of these methods.

Along these same lines, the prior art LUV techniques have, in general, produced liposomes of various sizes, as well as aggregates of liposomes, thus requiring the additional step of sizing the finished liposomes with a series of filters. Again, this makes the overall process more time consuming and complicated.

The fusion techniques include similar drawbacks. For example, the calcium ion/calcium chelating agent technique, like the solvent and detergent techniques, involves the use and subsequent removal of materials in addition to those actually making up the finished liposomes, in this case, the chelating agent and the added calcium ions. As with the solvents and detergents, these materials represent possible sources of contamination, limit the usefulness of the technique, and make the technique more complicated. Also, this technique requires that the composition of the liposomes includes some phosphatidylserine.

As to the freeze-thaw technique, this technique suffers from the drawback that the specific trapping capacity of the liposomes produced by the technique drops off sharply at phospholipid concentrations above about 20 mg/ml.

The SUV techniques have similar problems. For example, high energy sonication can cause oxidation and degradation of phospholipids and may damage solute molecules which one wants to capture in the interior space of the liposomes. Also, when performed using a sonication probe, high energy sonication can cause probe erosion, and if done with bath sonication in combination with radioactive materials, can produce a potentially hazardous aerosol. Low energy sonication is slow, can be destructive to phospholipid molecules, and cannot be used to prepare large quantities of liposomes. Further, the sonication approach results in low trapping efficiencies.

The infusion type SUV procedures suffer the same problems as the LUV infusion procedures. The high pressure French press technique has its own set of problems, including difficulties in making the technique repeatable, the need for post-preparation filtration to remove those MLVs which have not been converted to SUVs, the need for expensive and cumbersome equipment capable of withstanding the high pressures used, and contamination of the product by disintegration of components of the apparatus which occurs during processing of the liposomes. See, for example, Bosworth, et al., *Journal of Pharmaceutical Sciences*, 71:806 (1982). Also, this technique can only produce small liposomes having a low trapping efficiency.

SUMMARY OF THE INVENTION

In view of the foregoing state of the art, it is evident that there is a substantial and continuing need for an improved method for preparing unilamellar liposomes of both the SUV and LUV types.

It is the object of the present invention to provide such an improved technique. More particularly, it is an object of this invention to provide a simple, reproducible technique which can be performed with readily available and relatively inexpensive equipment, which has a minimum number of steps, which has a high output of liposomes per unit time, and which does not require that the components making up the liposomes be sonicated or combined with solvents, detergents or other extraneous materials.

To achieve the foregoing and other objects, the invention, in accordance with certain of its aspects, provides apparatus and a method for producing a population of substantially unilamellar liposomes which involves repeated extrusions at moderate pressures of previously formed liposomes through a filter having a pore size below a critical upper limit, specifically, below approximately 100 nm.

In this manner, the invention provides a variety of advantages over previously known systems for producing unilamellar liposomes, including the following: (1) the ability to form unilamellar vesicles from a wide range of lipids; (2) the ability to use high lipid concentrations (e.g., on the order of 300 umol/ml) so as to easily achieve high trapping efficiencies: (3) the ability to provide reproducible and very rapid production of unilamellar vesicles, and, in particular, large unilamellar vesicles, through the use of high extrusion flow rates and automatic or semi-automatic recycling of the liposomes through the filter: (4) the ability to produce liposomes of a desired size by using a single pore size filter with minimum filter clogging problems: (5) the ability to avoid the use of organic solvents and detergents; and (6) the ability to provide an overall relatively gentle process.

In some cases, rather than completely transforming a population of multilamellar liposomes into a population of substantially unilamellar liposomes, it is desirable to only partially decrease the lamellarity of the population without reaching the fully unilamellar stage. Filters having a pore size of about 100 nm are still used in accordance with this aspect of the invention, but with a reduced number of passes through the filter.

In accordance with some of its other aspects, the invention provides a method and apparatus for producing liposomes directly from a lipid powder or pellet by simply combining the powder or pellet with an aqueous buffer and then applying sufficient pressure to the lipid/buffer mixture to repeatedly pass it through a filter. If the filter has a pore size less than about 100 nm, substantially unilamellar liposomes are produced. If the filter has a pore size significantly above 100 nm, e.g., on the order of 200 nm, multilamellar liposomes are produced. Significantly, in either case, the liposomes are completely solvent free, in that, not even chloroform, as has been used in the past to produce MLVs, is required for liposome production in accordance with these aspects of the present invention.

The attainment of the foregoing and other objects and advantages of the present invention is described fully below in connection with the description of the preferred embodiments of the invention.

BRIEF DESCRIPTION OF THE DRAWINGS

In FIG. 1A, the liposome suspension is recycled through the filter by hand, while in FIG. 1B, the recycling has been partially automated.

FIGS. 8 and 9 show freeze-fracture micrographs of the vesicles of FIG. 7 processed through 50 nm and 30 nm filters, respectively. In each case, the upper portion of the figure (FIGS. 8A and 9A) was prepared after one extrusion ($-1$) through two stacked polycarbonate filters, and the lower portion (FIGS. 8B and 9B) after ten extrusions ($-10$).

DESCRIPTION OF THE PREFERRED EMBODIMENTS

Figure 1A:
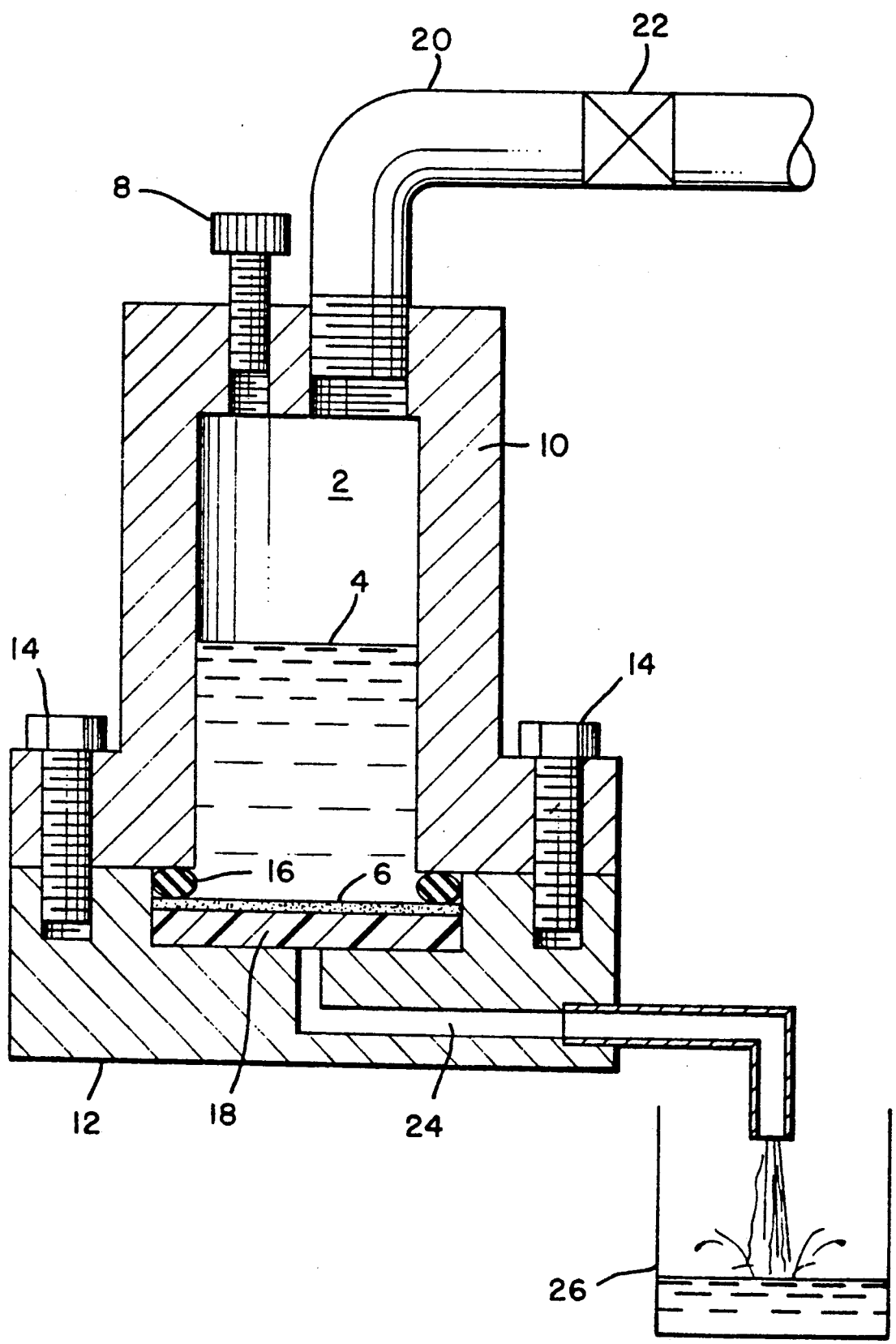
FIGS. 1A and 1B are schematic diagrams of apparatus suitable for practicing the present invention.

As described above, the present invention provides apparatus and a method for producing a population of substantially unilamellar liposomes wherein previously formed liposomes are subjected to multiple extrusions at moderate pressures through a filter having a pore size of less than or equal to about 100 nm.

The previously formed liposomes can have a variety of compositions and can be prepared by any of the techniques now known or subsequently developed for preparing liposomes.

For example, the previously formed liposomes can be formed by the conventional technique for preparing MLVs, that is, by depositing one or more selected lipids on the inside walls of a suitable vessel by dissolving the lipids in chloroform and then evaporating the chloroform, adding the aqueous solution to be encapsulated to the vessel, allowing the aqueous solution to hydrate the lipid, and swirling or vortexing the resulting lipid suspension to produce the desired liposomes. This technique employs the most gentle conditions and the simplest equipment and procedures known in the art for producing liposomes. Also, this technique specifically avoids the problems with sonication or the use of detergents, solvents (other than chloroform) or other extraneous materials, discussed above.

Alternatively, in accordance with one of the aspects of the present invention, the liposomes which are to be repeatedly extruded through the filter can be prepared by simply mixing a lipid powder or pellet and buffer together and then directly extruding that mixture through the filter. If the filter has a pore size of less than about 100 nm, this procedure produces unilamellar liposomes, while if the pore size is substantially greater than 100 nm, multilamellar liposomes are produced. In either case, the procedure eliminates the use of all solvents, including chloroform.

The filter is preferably of the type which has straight through channels. Polycarbonate filters of this type produced by Nuclepore, Inc., Pleasanton, Calif., have been found to work successfully in the practice of the present invention. In a typical procedure, the filter may have to be changed after the first two or three passes of the liposome suspension due to pore clogging. Clogging in general depends on such variables as lipid composition, purity and concentration, as well as on the pressure and flow rates used.

The most critical parameter in preparing unilamellar liposomes in accordance with the present invention is the size of the filter's channels. It has been found that unilamellar liposomes cannot be produced from multilamellar liposomes, no matter how many times the MLVs are passed through the filter, if the filter's pore size is significantly above about 100 nm, e.g., if the pore size is about 200 nm (see Example 2, infra). Accordingly, only filters having a pore size equal to or below about 100 nm can be used with this invention.

As illustrated in Example 6 below, the size of the unilamellar liposomes produced depends on the pore size of the filter used, the mean diameter being, in general, somewhat smaller than the pore size. If desired, the liposome's mean diameter, as well as their trapped volumes (ul per umol phospholipid), can be easily increased using the freeze-thaw procedure discussed above (see also Example 4, infra). Importantly, since this procedure does not involve the use of solvents, detergents or other extraneous materials, the increase in liposome size is not at the expense of introducing contamination and degradation problems. Vesicle size and trapped volumes can also be manipulated by varying other parameters of the system, such as, lipid composition.

The number of passes through the filter needed to produce the desired unilamellar liposomes depends on the filter characteristics (pore size, composition and geometry) and the materials from which the liposomes are to be made. As illustrated by Example 2, infra, five or more passes through a double stacked polycarbonate filter having a pore size of 100 nm are typically required to obtain unilamellar liposomes. Fewer passes may be needed for smaller pore sizes. For example, with 30 nm and 50 nm filters, two to four passes are in general sufficient to produce a substantially unilamellar population of liposomes (see Example 6, infra). Also, if the goal is only to reduce the lamellarity of the population, rather than to achieve substantial unilamellarity, fewer passes are needed. The appropriate number of passes for any particular system can easily be determined by persons of ordinary skill in the art by simply sampling the finished liposomes to determine when the desired degree of lamellarity has been achieved.

Passage of the liposomes through the filter is accomplished under pressure. Pressures of various magnitudes can be used depending upon the type and composition of the liposomes to be produced, the specific characteristics of the equipment employed, and the rate at which liposomes are to be produced.

Maximum pressures generally are limited by the pore size of the support used to hold the filter. For a filter support having a pore size of about 30 microns, pressures between about 100 and 700 psi have been found to work successfully. These pressures give high flow rates (on the order of 20-60 ml/min for a double stacked polycarbonate filter having a pore size of 100 nm), and produce intact unilamellar liposomes of a homogeneous size, e.g., 60-100 nm diameter liposomes for a 100 nm filter. With a filter support having a pore size smaller than 30 microns, higher pressures can be used.

As with the number of passages through the filter, the appropriate pressure for a particular system can be readily determined by persons skilled in the art by examining the finished liposomes to determine if they are substantially intact and unilamellar.

Pressures in the 100-700 psi range are also preferred because they allow for the extrusion of solutions having lipid concentrations on the order of about 300 umols phospholipid per ml without significant filter clogging. Prior art liposome sizing techniques employing polycarbonate filters used pressures less than 100 psi, and thus were limited to lipid concentrations of 60 umol/ml. The use of high lipid concentrations has resulted in trapping efficiencies on the order of 30% for the present invention. Rapid extrusion rates on the order of 20 ml/min and above are still achieved for such high lipid concentrations when pressures in the range of 300-500 psi are used.

Flow rates on the order of 20-60 ml/min do not represent the maximum flow rates that are achievable with the present invention, but merely represent rates consistent with convenient collection of the extruded material. Maximum flow rates are sensitive to the concentration of lipid, the history of the sample (i.e., whether it has been extruded one or more times), the pressure employed, and the nature of the lipids themselves. For example, "gel state" lipids cannot be extruded. Such lipids (e.g., dipalmitoyl phosphatidylcholine (DPPC)) must be heated above their gel to liquid crystalline transition temperature (41° C. for DPPC) before the extrusion process can proceed.

At increased pressure, the extrusion can be exceedingly rapid. For example, a 5 ml dispersion of 50 mg/ml egg phosphatidylcholine (EPC) has been extruded through a 100 nm pore size filter in less than 2 seconds at 500 psi, corresponding to a flow rate of at least 150 ml/min. This rate would be increased further by higher pressure or temperature.

Figure 1B:
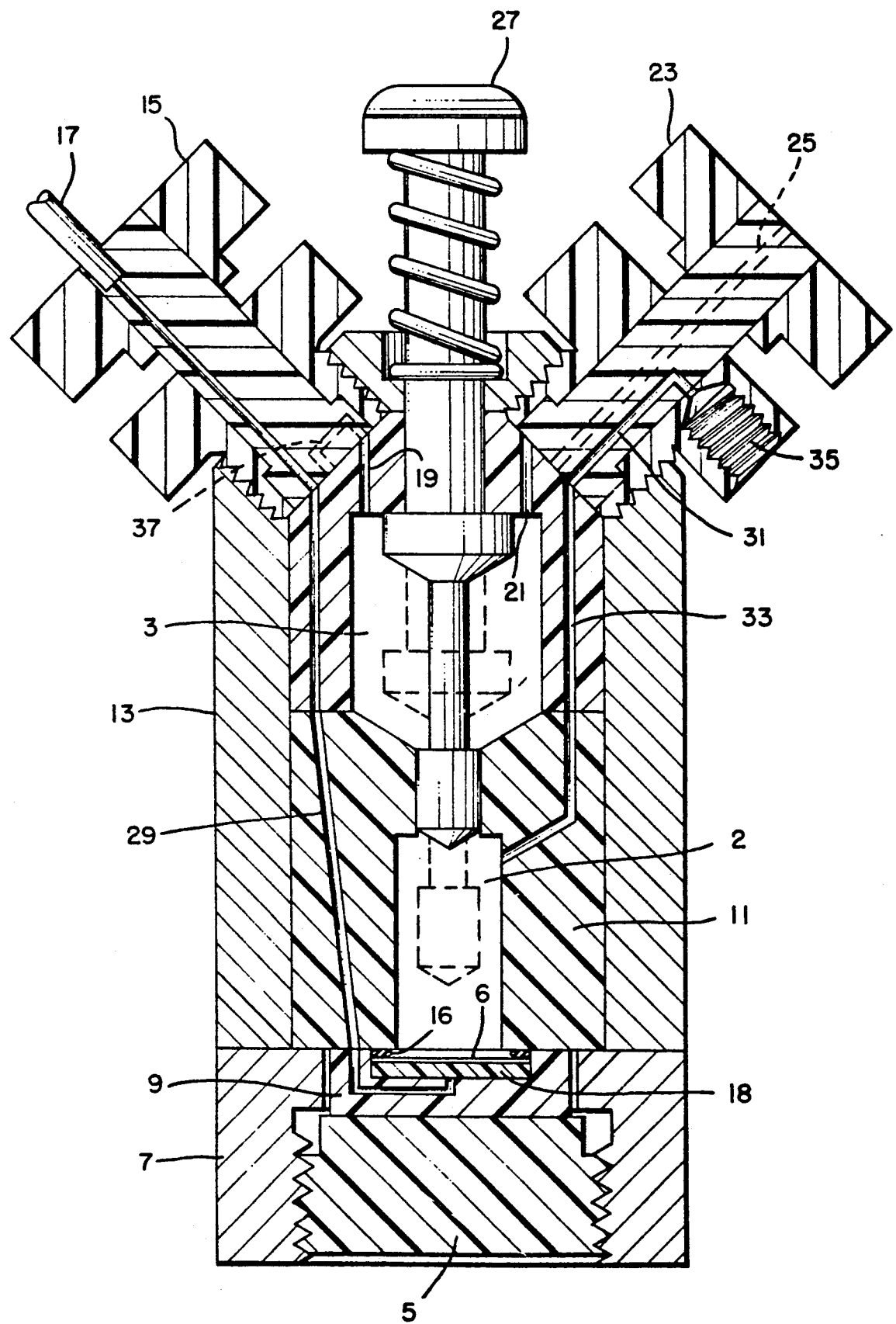

Suitable apparatus for practicing the present invention is shown in FIGS. 1A and 1B. As shown in FIG. 1A, liposome suspension 4 which is to be extruded through filter 6 is introduced into pressure chamber 2 by means of injection port 8. The injection port also serves as a release valve. Pressure chamber 2 is formed from upper portion 10 and lower portion 12 which are connected together by, for example, bolts 14. A seal between these portions and filter 6 is provided by O-ring 16. Preferably, the chamber is made of clear plastic so that the extrusion of the suspension from the chamber can be visually observed. The filter is supported within chamber 2 by filter support 18. In practice, it has been found convenient to use two stacked polycarbonate filters to form filter 6.

Pressure is supplied to chamber 2 by means of conduit 20 which is connected to a source of pressure, e.g., a high pressure nitrogen tank (not shown). Conduit 20 includes valve and regulator 22 for adjusting the pressure within chamber 2. The material extruded from filter 6 is removed from chamber 2 by means of conduit 24 and collected in receiving vessel 26. In practice, valve 22 is closed prior to the time all of the suspension has been extruded from chamber 2 so as to prevent high pressure gas from flowing through the system and blowing the suspension out of receiving vessel 26. After having been collected in vessel 26, the extruded material is repeatedly returned to chamber 2 by means of injection port 8, until the original population of liposomes has passed through filter 6 a sufficient number of times so as to substantially increase its unilamellarity.

FIG. 1B shows a modification of the apparatus of FIG. 1A wherein the recycling of the extrudate is partially automated. The apparatus shown in this figure is used as follows.

First, a filter 6 is installed in the apparatus by removing threaded retainer plug 5, filter support housing 9, and O-ring 16 from aluminum housing 7. A filter is then placed on the filter support and the components reassembled with plug 5 being tightened until O-ring 16 is compressed against inner PLEXIGLAS housing 11 contained within outer aluminum housing 13. If desired, a porous drain disc (not shown) can be placed under the filter.

A sample is then loaded into receiving chamber 3 by rotating load/recycle/discharge valve 15 until load/discharge tube 17 is aligned with inlet port 19, and by rotating pressure/vent valve 23 until vent port 25 is aligned with exhaust port 21. A sample can then be introduced into the receiving chamber through load/-discharge tube 17. Most conveniently, this is done by attaching a short length of flexible tubing and a hypodermic syringe to load/discharge tube 17.

Once the sample has been completely loaded into receiving chamber 3, it is transferred to pressure chamber 2 by depressing transfer valve 27. The sample is now ready for extrusion through filter 6. To perform the extrusion, pressure/vent valve 23 is rotated until gas inlet port 31 is aligned with pressure port 33, and load/-recycle/discharge valve 15 is rotated to a position where recycle port 37, formed in valve 15, is aligned at one end with inlet port 19 and at the other end with bypass port 29. Gas inlet port 31 is connected to threaded aperture 35 which serves to connect the apparatus to a valved and regulated external source of high pressure gas, e.g., a valved and regulated high pressure nitrogen tank (not shown).

Pressure is then applied to pressure chamber 2 causing the sample to pass from that chamber to receiving chamber 3 by way of filter 6, bypass port 29, recycle port 37, and inlet port 19. This accomplishes one extrusion of the sample through the filter. Flow from pressure chamber 2 to receiving chamber 3 can be visually observed through PLEXIGLAS housing 11, and the amount of pressure applied can be adjusted to achieve a gentle flow.

Once all of the sample has been transferred to receiving chamber 3, the valve on the external source of pressure is closed, and pressure/vent valve 23 is rotated to first bring vent port 25 into alignment with exhaust port 21 and then into alignment with pressure port 33, thus venting both receiving chamber 3 and pressure chamber 2. The sample can now be reintroduced to pressure chamber 2 by simply depressing transfer valve 27. With the sample in pressure chamber 2, the extrusion process is repeated following the procedures described above for the first extrusion. Note that with the sample in the receiving chamber and with both chambers having been vented, a new filter can be installed, if desired, following the procedures described above.

Once the receiving chamber—pressure chamber—receiving chamber cycle has been repeated the desired number of times, the sample is discharged from the apparatus through load/discharge tube 17 by first aligning gas inlet port 31 with exhaust port 21 and load/discharge tube 17 with inlet port 19, and then applying pressure to the system from the external pressure source. In practice, the external pressure is shut off before all of the sample has left chamber 3 to avoid high gas flows at the end of the evacuation. Rather than using load/discharge tube 17, the sample can also be removed by disassembling threaded retainer plug 5, filter support housing 9, and O-ring 16 from aluminum housing 7, and then depressing transfer valve 27 to cause the sample to flow into the pressure chamber and out the bottom of the apparatus.

If desired, the apparatus shown in FIG. 1B, or equivalent apparatus, can be equipped with conventional automatic fluid handling equipment and controls to achieve a completely automated process. Also, so as to be able to maintain the temperature of the sample above the gel to liquid crystalline transition temperature of the lipids used, the pressure chambers of whatever equipment is employed can be heated using a water jacket or similar device.

Without intending to limit it in any manner, the present invention will be more fully described by the following examples. In addition to these examples, filed simultaneously herewith is our commonly assigned application Ser. No. 622,502, entitled "Liposomes Having Defined Size Distributions," and now abandoned, which illustrates the use of the apparatus of the present invention to produce a population of liposomes having a defined size distribution. The pertinent portions of this application are incorporated herein by reference.

The materials and methods which are common to the various examples presented below are as follows.

Materials and Methods

Lipids

Egg phosphatidylcholine (EPC) and soya phosphatidylcholine (SPC) were isolated employing standard procedures (Singleton, et al., *Journal of the American Oil Chemical Society*, 42:53 (1965)). Corresponding varieties of phosphatidylethanolamine (PE) and phosphatidylserine (PS) were prepared from EPC and SPC to produce EPE, SPE, EPS and SPS (see Comfurius, P. and Zwaal, R.F.A. (1977) *Biochim. Biophys. Acta*, 488:36–42). The lipids from the soya source are considerably more unsaturated than those derived from EPC, due to the high content of linoleic acid in SPC (see Tilcock, C. P. S. and Cullis, P. R. (1981) *Biochim. Biophys. Acta*, 641:189–201). All lipids were more than 99% pure as determined by TLC. Acidic phospholipids (PS) were converted to the sodium salt form as described in Hope, M. J. and Cullis, P. R. (1980) *Biochem. Biophys. Res. Commun.*, 92:846–852. Cholesterol (Sigma, St. Louis) was used without further purification.

Determination of Trapped Volumes

To determine trapped volumes, multilamellar vesicles were prepared in accordance with the procedures described in Example 1, infra, but in the presence of 1 uCi of $^{22}$Na or $^{14}$C-inulin (NEN, Canada). Unilamellar liposomes were then prepared from the multilamellar liposomes, again following the procedures of Example 1.

An aliquot (100 ul) was then loaded onto a Sephadex G-50 column packed in a 1 ml disposable syringe, and vesicles eluted by centrifugation of the column at 500 g for 3 min. See Pick, U. (1981) *Arch. Biochem. Biophys.*, 212:186–194. In the case of $^{22}$Na this was sufficient to remove all the untrapped material. However, to remove all the untrapped inulin this procedure was either repeated once more or a single pass through an Ultragel column (LKB-ACA34) was employed. Aliquots of the eluted material were assayed for lipid phosphorus according to the method of Bottcher, C. J. F., Van Gent, C. M. and Pries, C. (1961) *Anal. Chim. Acta*, 24:203–204: trapped $^{22}$Na was determined employing a Beckman 8000 gamma counter and trapped $^{14}$C inulin was estimated using a Phillips PW-4700 liquid scintillation counter. Trapped volumes were then calculated as ul of trapped volume per umol of phospholipid.

Determination of Vesicle Size Distributions By Freeze-Fracture

Vesicle preparations were mixed with glycerol (25% by volume) and frozen in a FREON slush. Samples were fractured and replicated employing a Balzers BAF 400D apparatus, and micrographs of replicas were obtained using a Phillips 400 electron microscope. Vesicle size distributions were determined by measuring the diameter of fractured vesicles that were 50% shadowed according to the procedure of van Venetie et al., (1980) *J. Micros.*, 118:401–408.

$^{31}$P Nuclear Magnetic Resonance $^{31}$P NMR was employed to provide an indication of the extent to which the vesicle preparations were unilamellar. Specifically, $Mn^{2+}$ was added to the vesicle dispersion (3 ml, 30–60 umol phospholipid per ml in a 15 mm diameter NMR tube) at levels (5 mM) sufficient to broaden beyond detection the $^{31}$P NMR signal from those phospholipids facing the external medium. If the vesicles are large and unilamellar, then approximately 50% of the signal should remain following the addition of $Mn^{2+}$. The impermeability of the vesicles to $Mn^{2+}$ was demonstrated by following the timecourse of the signal intensity, which for the PC systems investigated was found to be stable over a period of days. Spectra were obtained employing a Bruker WP 200 NMR spectrometer operating at 81 MHz. Accumulated free induction decays corresponding to 1000 transients were collected using a 15 usec 90° radiofrequency pulse, gated proton decoupling and a 20 KHz sweep width. An exponential multiplication corresponding to a 50 Hz linebroadening was applied prior to Fourier transformation. Signal intensities were measured by cutting out and weighing spectra with triphenylphosphite (in a small central capillary in the NMR tube) as a reference.

Other Chemicals

Inulin, periodic acid, sodium-m-arsenite, tyramine, G-25 Sephadex, sodium cyanoborohydride, sodium borohydride, and cholesterol were obtained from Sigma. Ultrogel Ac34 was obtained from Pharmacia, carrier free $Na^{125}I$ (100 mCi/ml) was supplied by Amersham and iodogen was obtained from Pierce. All other chemical were of analytical grade.

Example 1

Preparation of Unilamellar Liposomes

This example illustrates the preparation of large unilamellar liposomes using the extrusion method of the present invention. For ease of reference, liposomes prepared in accordance with this technique are referred to herein by the acronym "LUVETs," i.e., Large Unilamellar Vesicles by Extrusion Techniques.

Large multilamellar vesicles (MLVs) were prepared by the conventional process as follows. First, lipid dissolved in chloroform was dried down and deposited as a film on the inside of a test tube. The MLVs were then formed by simply adding an aqueous buffer of 150 mM NaCl, 20 mM HEPES, pH 7.5, to the test tube and hydrating the lipid by vortex mixing.

The resulting MLV dispersion (2-10 ml) was then transferred into the pressure chamber of the apparatus shown in FIG. 1A, equipped with two stacked standard 25 mm polycarbonate filters having a 100 nm pore size (Nuclepore, Inc., Pleasanton, California, Catalog #110605). Nitrogen pressure was applied to the chamber via a standard gas cylinder fitted with a high pressure (0–4000 psi) regulator. The vesicles were extruded through the filter employing pressures of 100–700 psi resulting in flow rates of 20–60 ml/min, and were collected and re-injected. Repetition of the extrusion procedure five or more times resulted in the production of large unilamellar liposomes having diameters of approximately 70 nm as measured by freeze fracture. The overall extrusion process including recycling generally took fifteen minutes or less.

The following examples describe in detail the size, unilamellarity, trapped volume, trapping efficiency and influence of various lipid compositions on liposomes produced by the foregoing procedure. Also, the effects of a freeze-thaw procedure on trapped volume and the criticality of filter pore size are illustrated.

Example 2

Criticality of Filter Pore Size

This example demonstrates the criticality of filter pore size in producing unilamellar liposomes, and, in particular, the criticality of using a filter having a pore size of less than or equal to about 100 nm.

Figure 2:
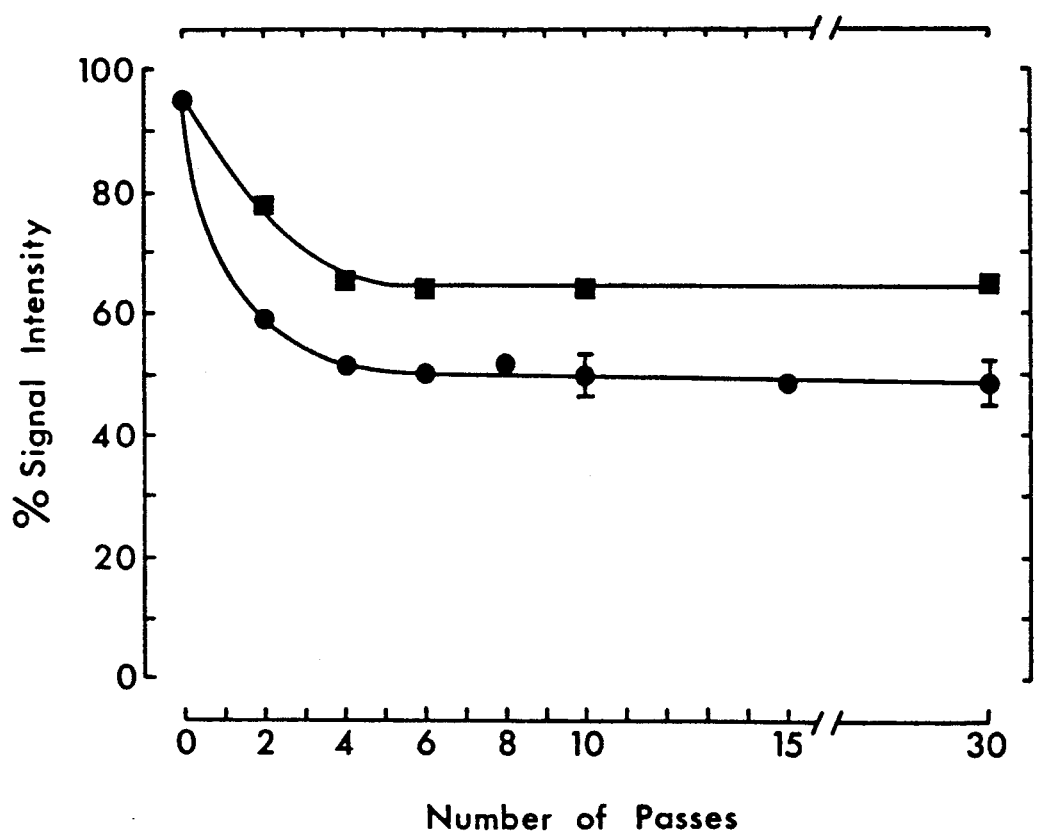
FIG. 2 shows the $^{31}P$ NMR signal intensity arising from egg phosphatidylcholine (EPC) multilamellar vesicles (in the presence of 5 mM $MnCl_2$) as a function of the number of extrusions through polycarbonate filters with 100 nm (circles) and 200 nm (squares) pore sizes. The error bars represent standard deviations ($n=6$ for the point at 10 extrusions through the 100 nm filter; $n=3$ for the point at 30 extrusions). All other experimental points represent the average obtained from two separate experiments. The lipid concentration in all cases was between 30 and 60 umol/ml.

EPC MLVs were prepared in accordance with the procedures described in Example 1 and then repeatedly passed through polycarbonate filters having pore sizes of 100 and 200 nm. The unilamellarity of the resulting liposomes was determined using the $^{31}$P NMR technique described above. The results are shown in FIG. 2.

As shown in that figure, for vesicles passed through the 200 nm filter, the signal intensity drops to approximately 65% after five passes through the filter and then remains relatively constant. For the 100 nm filter, on the other hand, the signal drops to approximately 50% after five or more passes.

Since a drop in signal intensity to about 50% indicates that the liposomes are substantially unilamellar, while a drop to only 65% indicates substantial multilamellarity, these results show that the 100 nm filter succeeds in producing unilamellar liposomes, as desired, while the 200 nm filter continues to produce significant amounts of multilamellar liposomes irrespective of the number of passes through the filter.

Figure 3:
FIG. 3 shows four freeze-fracture micrographs of vesicles prepared by repeated extrusion of multilamellar vesicles of varying lipid composition through polycarbonate filters: (a) soya phosphatidylcholine (PC) MLVs extruded through a 100 nm filter; (b) soya PC—soya PS (1:1) MLVs extruded through a 100 nm filter; (c) soya PE—soya PS (1:1) MLVs extruded through a 100 nm filter; (d) soya PC MLVs extruded through a filter with a 200 nm pore size. The arrow in part (d) indicates a cross fracture revealing inner lamellae. All micrographs have the same magnification and the direction of shadowing is indicated by the arrowhead in the bottom right corner of each section. In each case, the extrusion procedure was repeated 10 times on lipid systems containing 40–70 umol/ml phospholipid.
Figure 3:
Figure 3:
Figure 3:

This conclusion is confirmed by the freeze-fracture micrographs shown in FIG. 3. As shown in that figure, vesicles formed from SPC, SPC-SPS (1:1) and SPE-SPS (1:1) (FIGS. 3(*a*), (*b*) and (*c*), respectively) using a 100 nm filter do not exhibit a significant number of cross-fractures (less than 0.1%) indicating the absence of inner lamellae. In contrast, cross-fractures are readily observable for SPC vesicles processed through a 200 nm filter (FIG. 3(*d*)).

These results clearly establish that in accordance with the present invention, unilamellarity depends upon the use of a filter having a pore size on the order of 100 nm or below.

Example 3

LUVET Diameters, Trapped Volumes and Unilamellarity

This example demonstrates that the procedures of the present invention when used with 100 nm filters reproducibly result in the production of a relatively homogeneous population of LUVs for a variety of lipid constituents. Vesicle diameters and trapped volumes were determined by the methods described above. The results are shown in FIG. 4 and Table I, infra.

Figure 4:
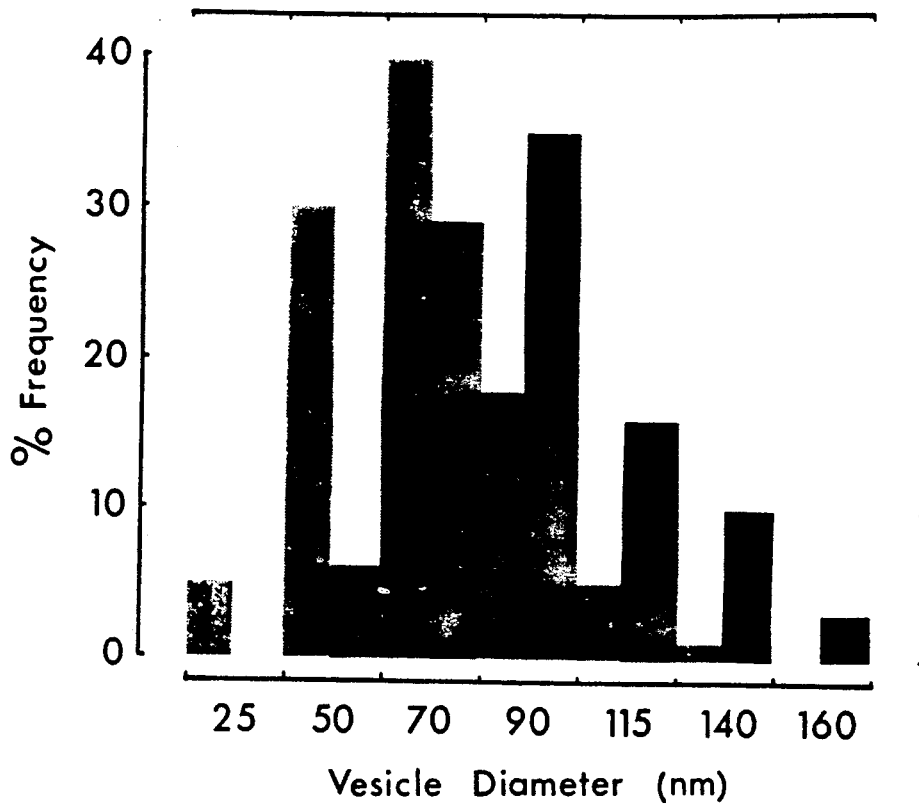
FIG. 4 shows the size distribution of soya PC vesicles obtained after 10 extrusions through a polycarbonate filter with a 100 nm pore size. The vesicle diameters were measured from freeze fracture micrographs employing the technique of van Venetie et al, (1980) *J. Micros.*, 118:401–408. The black and half-tone columns represent vesicles that did and did not undergo freeze-thaw cycling, respectively.

The half-tone columns in FIG. 4 show the vesicle diameters measured for SPC LUVETs which were prepared by passing MLVs prepared in accordance with Example 1 through two (stacked) 100 nm pore size filters ten times. Table I shows in summary form the measured mean diameters and mean trapped volumes for this and other lipid compositions. As a control, EPC LUVs were prepared by two procedures (octylglucoside detergent dialysis and reverse phase evaporation) which are generally accepted to produce unilamellar vesicles, and the LUVs so produced were then extruded ten times through two (stacked) 100 nm pore size filters. See Mimms, L. T., Zampighi, G., Nozaki, Y., Tanford, C. and Reynolds, J. A. (1981) *Biochemistry*, 20:833–840 and Szoka, F. and Papahadjopoulos, D. (1980) *Ann. Rev. Bioeng.*, 9:467–508. The results for these controls are also shown in Table I. (It is of interest to note with regard to the generality of the present invention that when the octylglucoside procedure was employed to make vesicles consisting of EPC/cholesterol (1:0.25), multilamellar vesicles were formed, whereas with the procedure of the present invention and the same lipid constituents, substantially unilamellar vesicles were formed.)

The vesicle diameter distribution shown in FIG. 4 can be used to determine calculated values for trapped volumes and amount of inner monolayer phospholipid by assuming (1) an area per phospholipid molecule, e.g., 0.6 nm$^2$ (see Schieren, H., Rudolph, S., Finkelstein, M., Coleman, P. and Weissman, G. (1978) *Biochim. Biophys. Acta.*, 542:137–153); (2) a bilayer thickness, e.g., 4 nm (see Blaurock, A. E. (1982) *Biochim. Biophys. Acta.*, 650:167–207); and 3) that the vesicles are unilamellar. These calculated values can then be compared with the experimentally observed trapped volumes and amounts of inner monolayer phospholipid to determine the proportion of unilamellar vesicles present.

Following this approach for the vesicle size distribution shown in FIG. 4 (half tone), it was determined that such a vesicle population (if unilamellar) would have an "inner monolayer" signal intensity (after the addition of Mn$^{2+}$) of approximately 43% of the original intensity and that the trapped volume would be approximately 1.6 ul/umole. This is in reasonable agreement with the measured values of sequestered phospholipid (48%) and trapped volume (1.2 ±0.2 ul/umol) in view of the number of assumptions made, and, in particular, in view of the difficulty in estimating the area per phospholipid molecule which can greatly affect the trapped volume expressed as ul trapped per umole of phospholipid.

Comparing the calculated trapped volume value of 1.6 ul/umole with the experimental data shown in Table I reveals that LUVETs composed of SPC and EPC exhibit trapped volumes smaller than those expected, while if a charged phospholipid species such as phosphatidylserine is present, the theoretical trapped volume is achieved.

Two possible reasons for the low trapped volumes observed for EPC and SPC LUVETs are that there are a significant number of multilamellar vesicles present in the population, or that there are a greater proportion of small vesicles present than estimated from the freeze-fracture micrographs. The freeze-fracture results suggest that the number of multilamellar vesicles is very small (less than 2%), even if it is assumed that only 5% of fractured multilamellar systems exhibit a cross-fracture (see R. G. Miller, *Nature*, 287:166 (1980)). On the other hand, an underestimation of the number of small vesicles is likely.

Moreover, as shown in Table I, the trapped volumes measured for EPC LUVs produced by the octylglucoside detergent dialysis procedure and the reverse phase evaporation procedure, which were subsequently extruded 10 times through a filter with a 100 nm pore size, are comparable to the trapped volumes obtained for the EPC LUVETs.

These observations, taken together, demonstrate that the great majority of vesicles produced by the extrusion technique of the present invention are unilamellar, even though the measured trapped volume in certain cases is smaller than the calculated value.

To establish that the procedures of the present invention when used with filters having a pore size of 100 nm produce LUVs, as opposed to SUVs, calorimetric studies were conducted on MLVs and LUVETs composed of 6:0/16:0 PC (dipalmitoylphosphatidylcholine—DPPC).

SUVs composed of saturated phospholipids, such as, DPPC, are known to exhibit a reduction in the gel-liquid crystalline transition temperature ($T_c$) and a broadening of the transition due to their highly curved membranes. This high curvature is generally considered undesirable because it results in increased disorder in the membrane's hydrocarbon region (see Schuh, J. R., Banerjee, U., Muller, L. and Chan, S. I. (1982) *Biochim. Biophys. Acta*, 687:219–225).

Figure 5:
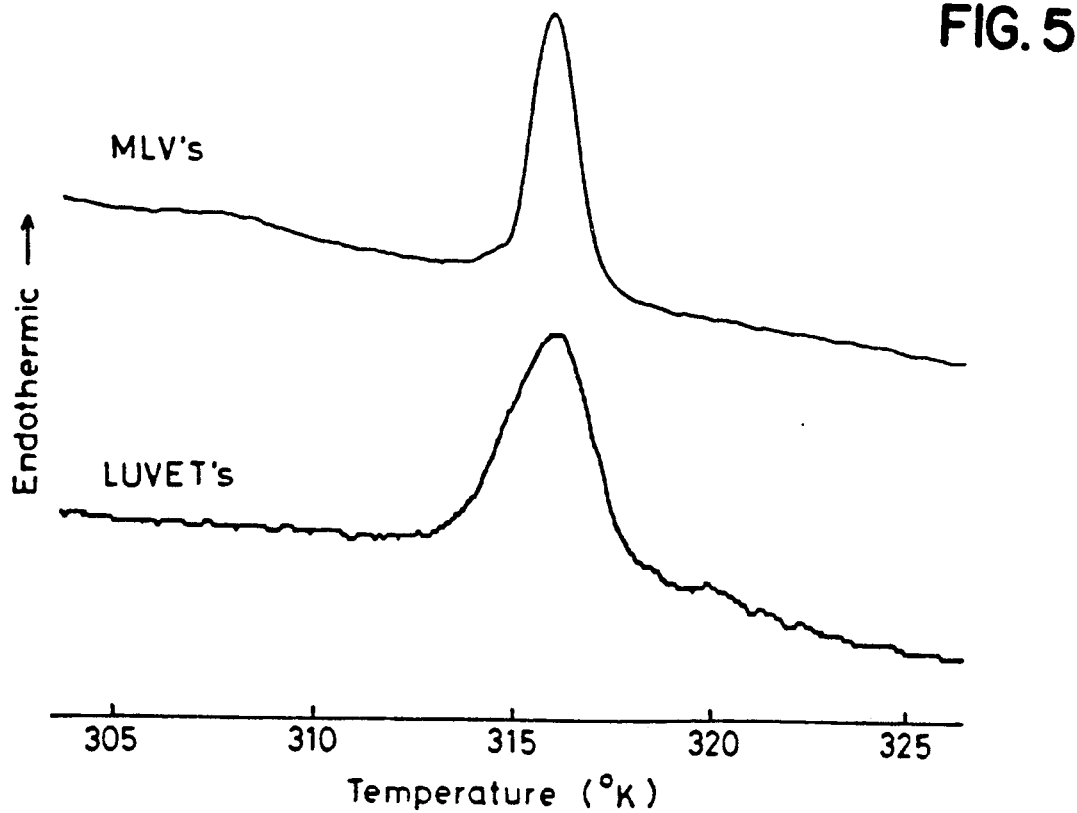
FIG. 5 shows the calorimetric behavior of hydrated dipalmitoylphosphatidylcholine (DPPC) in large multilamellar vesicles (MLVs) and in large unilamellar vesicles prepared by the extrusion technique of the present invention (LUVETs). The MLVs were formed by vortexing a dry lipid film in the bottom of a test tube in the presence of a NaCl buffer at 50° C., whereas the LUVETs were formed by repetitive extrusion (10 times) of the MLVs (50 mg lipid/ml) through 100 nm pore size polycarbonate filters at 50° C. Scan rates of 2.0° K./min were employed.

In order to ascertain whether the LUVETs produced by the present invention are sufficiently large to avoid the problems arising from highly curved membranes, $T_c$ values were calorimetrically measured for MLVs and LUVETs prepared in accordance with the procedures of Example 1. The results are shown in FIG. 5.

As illustrated in this figure, the MLVs and LUVETs exhibit very similar values of $T_c$. These values are consistent with those reported in the literature. See Ladbrooke, B. D. and Chapman, D. (1969) *Chem. Phys. Lipids*, 3:304–367. They are in direct contrast to the behavior observed for sonicated DPPC vesicles, which exhibit a broadened gel-liquid crystalline transition which occurs some 4° C. below the melting temperature of the multilamellar systems. See van Dijck, P. W. M., de Kruijff, B., Aarts, P. A. M. M., Verkleij, A. J. and de Gier, J. (1978) *Biochim. Biophys. Acta*, 506:183–191. Accordingly, the unilamellar liposomes prepared by the procedures of the present invention using filters with a 100 nm pore size are properly classified as LUVs, rather than SUVs.

To test the structural integrity of the liposomes produced by the extrusion process of the present invention, LUVETs were prepared in accordance with the procedures of Example 1, but with a buffer having a NaCl concentration of 1 M, instead of 150 mM. After preparation, the liposomes were placed in distilled water creating a large osmotic pressure difference across the liposomes' membranes. Using arsenazo III as a marker for liposome leakage, essentially no leakage was found under these severe test conditions.

Example 4

Use of Freeze-Thaw Cycles to Increase Trapped Volume

This example illustrates the use of a freeze-thaw procedure to increase the trapped volumes of the unilamellar liposomes produced by the present invention.

SPC and EPC LUVETs prepared in accordance with the procedures of Example 1 were subjected to two freeze-thaw cycles (employing liquid nitrogen) followed by extrusion through new 100 nm pore size filters. Specifically, the LUVETs were placed in a plastic vial, and the vial placed in liquid nitrogen for approximately 1 minute. The frozen LUVETs were then thawed in water at room temperature for approximately 5 minutes. The thawed solution was extruded 3 times through new 100 nm filters, after which the freeze-thaw-extrude process was repeated a second time.

Summary results for the process are given in Table I. Details of the size distribution of freeze-thawed SPC LUVETs is given in FIG. 4 (solid columns).

As shown in FIG. 4, the mean diameter of the SPC LUVETs increased by approximately 20 nm. The calculated trapped volume for this vesicle distribution is 2.3 ul/umole which is in excellent agreement with the measured value of 2.2±0.1 ul/umol (Table I).

Even higher trapped volumes were achieved using a soya PC system wherein freeze-thawing of LUVETs prepared by extrusion (10 times) through the 100 nm pore size filters, followed by extrusion (three to four times) through 200 nm pore size filters, resulted in trapped volumes on the order of 10 ul/umol phospholipid.

Example 5

LUVET Trapping Efficiency

An important parameter of LUV preparations is their trapping efficiency. This is especially so when the agents to be trapped are either expensive, as is the case for many drugs, or have low solubilities.

In connection with the present invention, it has been found that the overall process can be made to have trapping efficiencies on the order of 30%, notwithstanding the relatively low trapped volumes of the vesicles produced, by simply increasing the lipid concentration of the solutions used to prepare the LUVETs.

Figure 6:
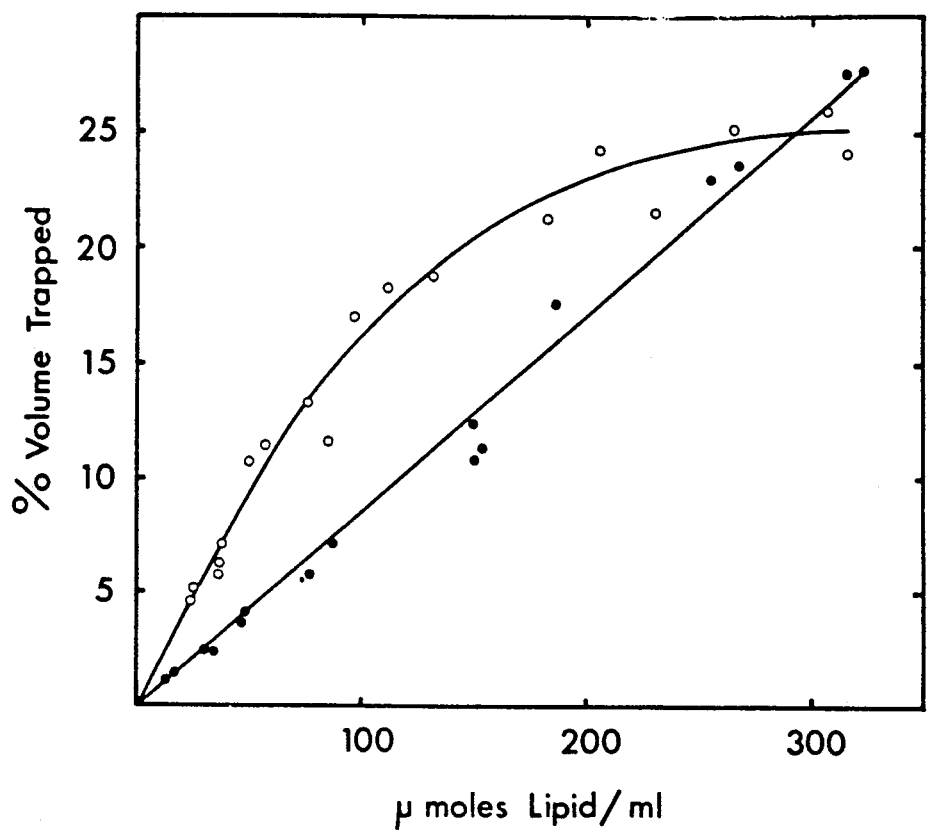
FIG. 6 shows the trapping efficiency as a function of lipid concentration for liposomes prepared in accordance with the present invention both with (open circles) and without (closed circles) freeze-thawing. $^{14}C$-inulin was used as a trap marker.

This effect is demonstrated in FIG. 6 where the percentage of aqueous volume trapped inside the LUVETs is plotted against lipid concentration for LUVETs prepared in accordance with the procedures of Example 1 (solid circles) and using the freeze-thaw procedure of Example 4 (open circles).

Preparation of LUVETs at lipid concentrations of 300 umoles/ml is easily accomplished, giving rise to trapping efficiencies on the order of 30% as shown in the figure. It is interesting to note that the freeze-thaw cycle only gives rise to significant increases in trapped volume per umol of lipid at lipid concentrations below 200 umol/ml. Similar observations have been reported by Pick, U. (1981) *Arch. Biochem. Biophys.*, 212:186-194.

Example 6

Use of Filters Having Pore Sizes Less Than 100 nm

This example illustrates the effects of using filters having pore sizes less than 100 nm on the size of the liposomes produced and on the number of passes through the filter needed to achieve substantial unilamellarity.

Figure 9:
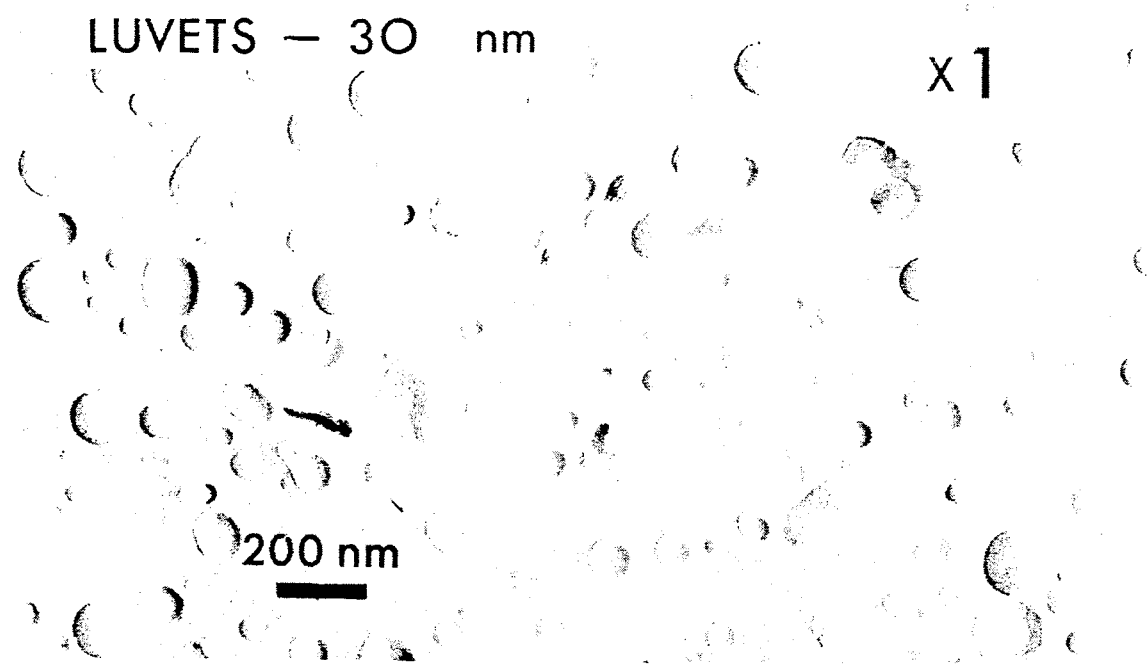
Figure 9:
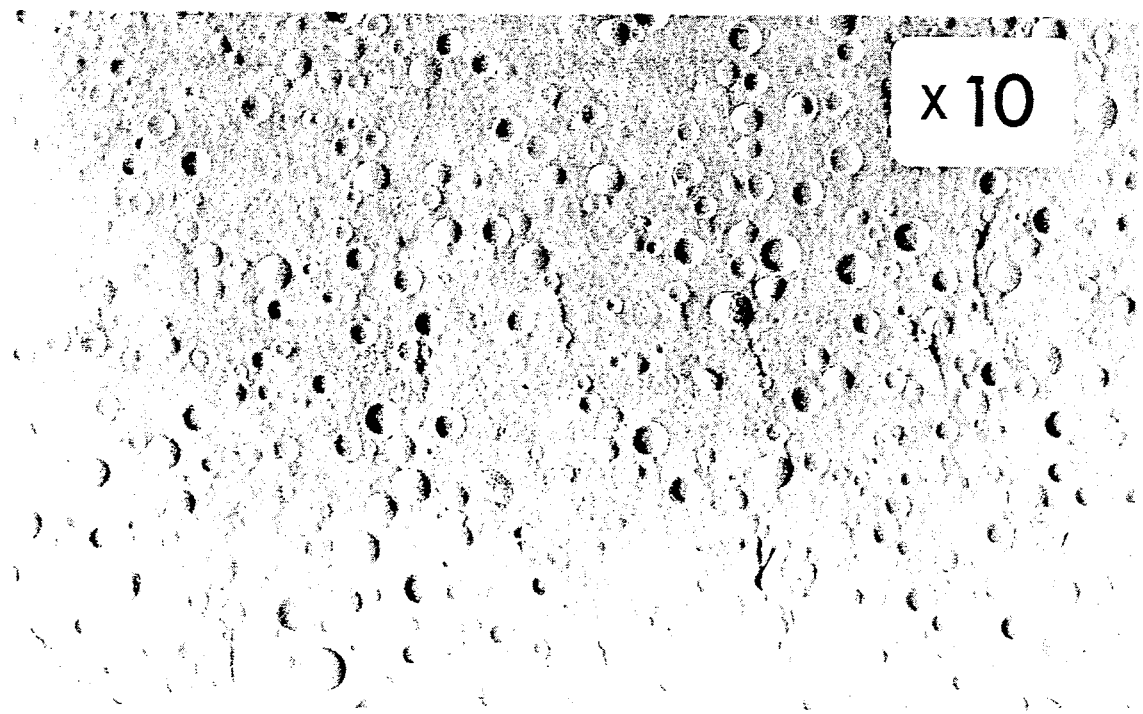

MLVs were prepared in accordance with the procedures of Example 1 using egg PC at a concentration of 100 mg/ml and using a buffer of 150 mM NaCl and 20 mM Hepes (pH 7.5). The dispersion was passed ten times through two stacked polycarbonate filters having a pore size of either 50 nm or 30 nm using the apparatus of FIG. 1A. Aliquots were taken after one and after ten passes through the extrusion device and used to prepare freeze-fracture micrographs as described above. Samples (4ml, 25 mg phospholipid per ml) were also taken after various numbers of passes and analyzed by $^{31}P$ NMR using $Mn^{2+}$ as described above. The results are shown in FIGS. 7-9.

Figure 7:
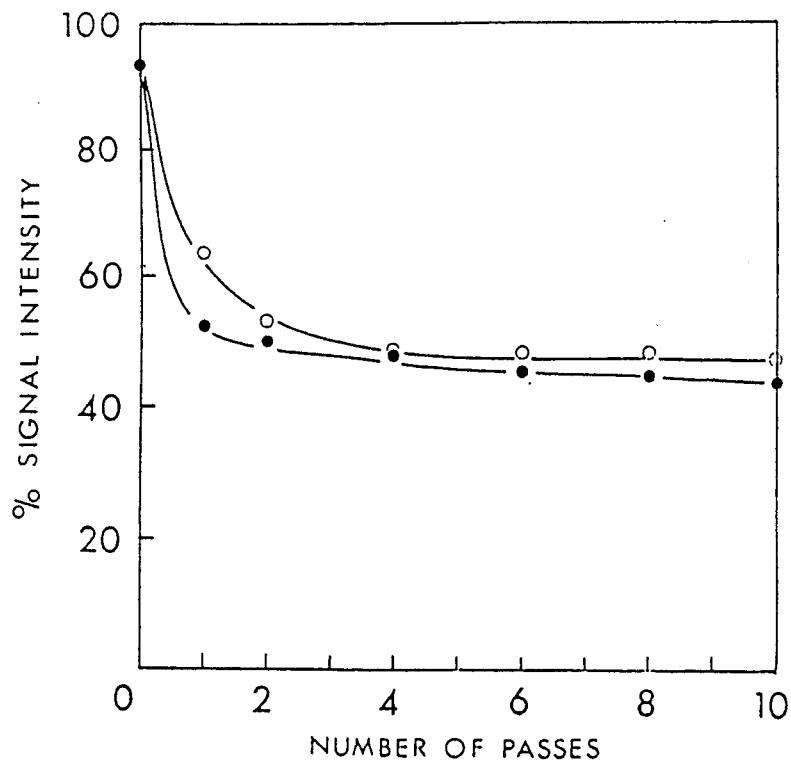
FIG. 7 shows the $^{31}P$ NMR signal intensity arising from egg phosphatidylcholine (EPC) multilamellar vesicles (in the presence of 5 mM $MnCl_2$) as a function of the number of extrusions through polycarbonate filters with 50 nm (open circles) and 30 nm (solid circles) pore sizes. The lipid concentration in all cases was 100 mg/ml.

As shown in FIG. 7, vesicles extruded once through the 50 nm filters lost 37 percent of their $^{31}P$ NMR signal upon addition of $Mn^{2+}$, while vesicles extruded once through the 30 nm filters lost 47.5 percent. This indicates that the vesicles passed through the 50 nm filters are larger and/or more multilamellar than those passed through the 30 nm filter, a result which is confirmed by the freeze-fracture micrographs shown in FIGS. 8 and 9. Comparing the upper portions of those figures (FIGS. 8A and 9A) reveals that the liposomes which were passed once through the 50 nm filters are larger and more irregular than those which were passed once through the 30 nm filters.

After ten passes, the $^{31}P$ NMR signal intensities dropped by 53 and 56 percent for the 50 nm and 30 nm filters, respectively. This indicates that both filters were producing essentially the same size liposomes. This was confirmed by analysis of freeze-fracture micrographs which revealed that both populations had an average diameter of 44±14 nm, i.e. a diameter characteristic of SUVs. As illustrated by FIGS. 8B and 9B, in each case, the population produced was homogeneous.

Comparing the curves of FIG. 7 with the curve for the 100 nm filter in FIG. 2 reveals that the $^{31}P$ NMR signals tend to level off faster for the filters with smaller pore sizes. Accordingly, fewer passes through the extrusion apparatus are required to achieve a population of substantially unilamellar liposomes with the smaller pore size filters.

Example 7

In Vivo Distribution of Unilamellar Liposomes

This example illustrates the use of liposomes prepared in accordance with the present invention to deliver entrapped material in vivo. In particular, it illustrates for a rat model system the administration and subsequent in vivo distribution of $^{125}I$-tyraminyl-inulin ($^{125}ITI$) containing LUVETs prepared in accordance with Example 1 above.

Tyraminyl-inulin was prepared as follows. Inulin (1.0 g) was dissolved in 90.0 ml distilled $H_2O$ and cooled to 4° C., 10 ml (fresh) 0.1 M periodic acid was added and the solution was incubated at 4° C. for 15 minutes in the dark. Periodate consumption was assayed by the arsenite method indicating approximately two oxidations per inulin molecule (see Dyer, J. in *Methods of Biochemical Analysis*, P. Glick (Ed.), Vol. 3, p. 111, Interscience (1956)). The reaction was terminated by neutralization with $Ba(OH)_2$ and the periodate and iodate salts were removed by centrifugation. To the supernatant 4.3 g $NaH_2PO_4$ and 0.55 g tyramine were added and the pH was adjusted to 7.5 with 1.0 M HCL. Subsequently, NaBH$_3$CN (0.25 g) was added and the solution was stirred for 4 hr at room temperature. Remaining aldehyde groups were reduced by careful addition of 0.2 g NaBH$_4$ and the solution was stirred for another hour at 27° C. Aliquots (25 ml) were degassed under reduced pressure and applied to a 1.5×80 cm Sephadex G-25 column previously equilibrated with H$_2$O at 4° C. The flow rate was adjusted to 10 ml/hr and 4 ml fractions were collected. The fractions were assayed for tyramine by monitoring the absorbance at 279 nm and for sugar by employing the anthrone reagent technique (see Roe, J. H. (1955) J. Bio. Chem., 212:335-343). The sugar containing fraction eluted in the void volume and had a constant tyramine:inulin mole ratio of 0.6. The adduct was completely separated from the free tyramine and other salts as determined by rechromatography on Sephadex G-25. The peak fractions were lyophilized giving an 80% yield, based on inulin.

The tyraminyl-inulin adduct was iodinated as follows. 2.5 mg of the tyraminyl-inulin adduct were dissolved in 0.2 ml HEPES (20 mM), NaCl (145 mM) pH 7.4 (HEPES buffered saline; HBS) and placed in a 1.5 ml stoppered vial in which 40 ug iodogen had been previously deposited from 300 uL CHCl$_3$. Then carrier free Na$^{125}$I (4 mCi, 100 mCi/ml) was added and the reaction allowed to proceed for 45 min at room temperature. The solution was then transferred to a vessel containing 10 ul 0.1 M Na$_2$S$_2$O$_5$, 0.05 M KI which was then applied to a G-25 column (1×20 cm) equilibrated with HBS. Fractions (0.5 ml) were collected and the $^{125}$I containing fractions eluting in the void volume (2.5 ml) were pooled. The resulting $^{125}$I-tyraminyl-inulin ($^{125}$ITI) solution routinely contained 1 uCi/uL $^{125}$I, where less than 0.01% was in the free iodide form (less than 0.01% was CHCl$_3$ extractable when made to 1.2% H$_2$O$_2$ and 0.4% KI) and over 99% of the material eluted as one peak in the void volume on re-chromatography employing Sephadex G-25. In all studies the material was used within 2 weeks of production.

Liposomes loaded with $^{125}$ITI were prepared in accordance with the procedures described above. Specifically, 30 umol egg phosphatidylcholine (EPC) and 30 umol cholesterol were dried down from CHCl$_3$. The resulting lipid film was dispersed in 1 ml HBS containing 1 mCi $^{125}$ITI by vortex mixing. The multilamellar systems thus produced were then extruded 10 times through two (stacked) polycarbonate Nuclepore filters (100 nm pore size) under N$_2$ pressure (200-400 psi). Aliquots (0.1 ml) of the LUVETs were applied to an Ultrogel Ac34 column (1 ml) previously equilibrated with HBS. The lipid containing fractions were pooled and rechromatography indicated that more than 97% of the $^{125}$ITI was "trapped" in the vesicles. The resulting liposome preparation had a trap volume of 0.9 ul/umol phospholipid as calculated from lipid phosphate analysis and entrapped $^{125}$ITI (see Fiske, C. H. and Subbarow, Y. (1925) J. Biol. Chem., 66:375-379). The average radius of these vesicles was 70 nm. The LUVETs containing $^{125}$ITI were diluted to 0.5 umol phospholipid in 200 ul of HBS, stored at 4° C. and used within 2 days of preparation.

The LUVETs were administered to female Wistar rats (150-200g), which were fed ad libitum prior to and during the experiments, by lightly anesthetizing the animals with ether and then injecting 200 ul HBS containing approximately 0.5 uCi 125ITI encapsulated in LUVETs (0.5 umol phospholipid) via the tail vein. The rats were allowed to recover in metabolic cages where the urine and feces were collected. At various times post injection the rats were anesthetized with ether and sacrificed by exsanguination via the vena cava. Blood was collected in a syringe containing 200 uL 200 mM EDTA and recovery was approximately 85% assuming 4.9 ml blood/100 g rat. The heart, liver, lung, spleen and kidney were removed and the urine remaining in the bladder was collected. The carcass was then dissolved in 200 ml 9 M NaOH at 70° C. overnight. Aliquots of carcass digest and samples of tissues were then assayed for the presence of $^{125}$I.

Figure 10:
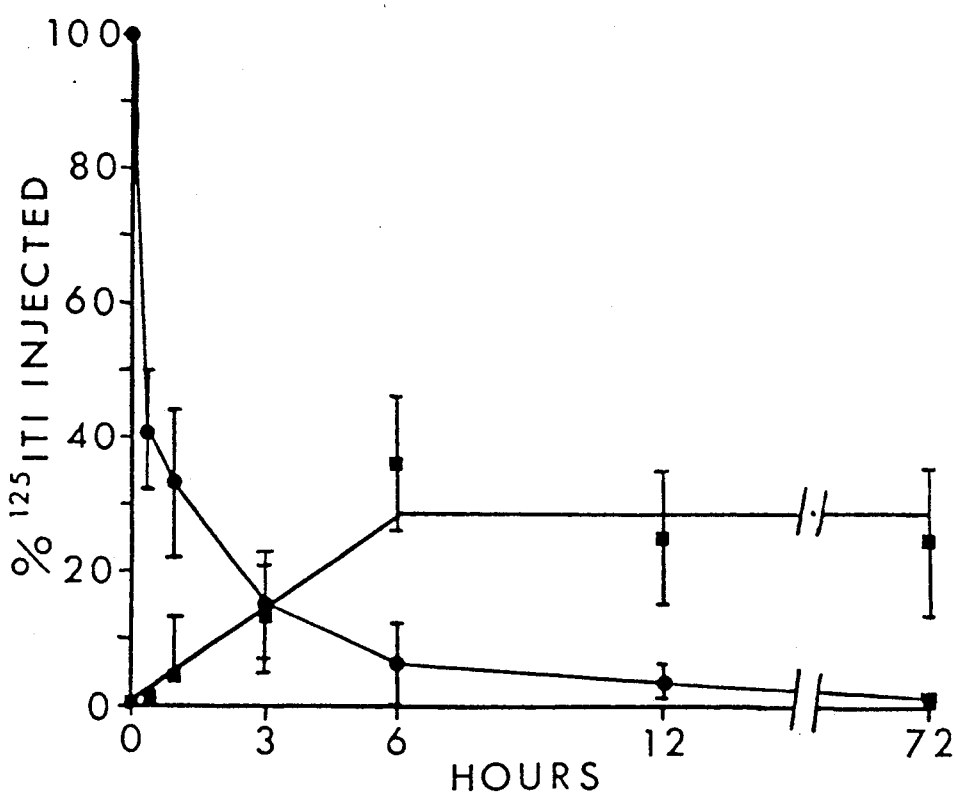
FIG. 10 shows the clearance of $^{125}I$-tyraminyl-inulin ($^{125}ITI$) entrapped in egg phosphatidylcholine (PC)—cholesterol (1:1) LUVETs from the rat circulation (circles) and subsequent excretion in the urine (squares). The LUVETs were prepared in accordance with the present invention and were injected into the tail vein of 150–175 g female Wistar rats at a dose level of 0.5 umol phospholipid in 100 ul HBS. Urine was collected in metabolic cages. Blood was withdrawn and the animals sacrificed at the indicated times and the total amount of $^{125}ITI$ in the blood calculated assuming 4.9 ml blood per 100 g rat. Results are expressed as percentages of the total $^{125}ITI$ injected $\pm$s.e. ($n=4$).

FIG. 10 illustrates the clearance from the circulation of the LUVETs and the subsequent appearance of inulin in the urine. As shown in that figure, the encapsulated material in the circulation is initially rapidly reduced to approximately 40% of the injected levels, and thereafter decays with a much longer half-life (approximately 3 hr). Further, only 30% of the injected dose is eventually found in the urine even after 3 days. This latter result clearly indicates tissue uptake and retention of LUVET encapsulated $^{125}$ITI.

Figure 11:
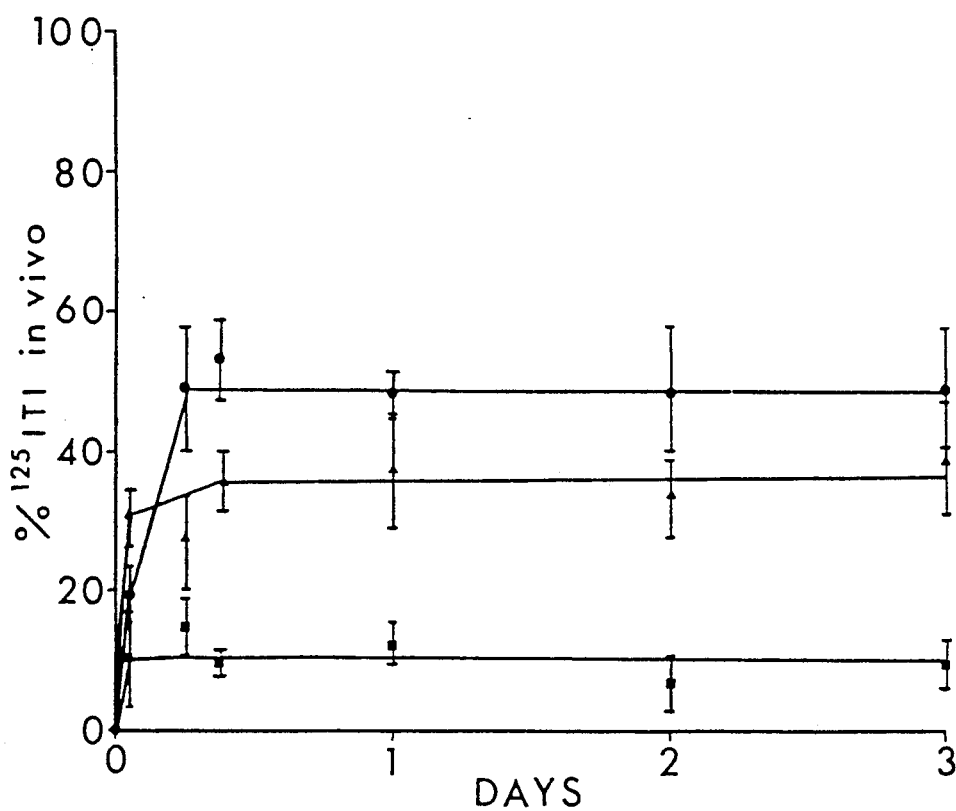
FIG. 11 shows the long term tissue distribution of the LUVETs of FIG. 10. The symbols correspond to liver (circles): carcass (triangles) and spleen (squares). Results are expressed as percentages of total $^{125}ITI$ in vivo (total $^{125}ITI$ injected minus amount excreted) $\pm$s.e. ($n=4$).

The actual tissue distributions are shown in FIG. 11 where approximately 50% of the in vivo accumulated by the liver, approximately 10% by the spleen and the rest is found in the carcass. Less than 3% $^{125}$ITI was found in the heart, lung and kidney at any time post injection (data not shown).

The tissue distributions observed are similar to those previously observed with liposomes produced by other methods (see, for example, Abra, R. M. and Hunt, C. A. (1981) Biochim. Biophys. Acta, 666, 493-503), thus demonstrating that the liposomes of the present invention are equivalent with regard to in vivo behavior to prior art liposomes.

Example 8

Solvent Free Production of Liposomes

This example illustrates the production of liposomes directly from a lipid powder or pellet and buffer without the use of any solvents or other extraneous materials.

One hundred mg of EPC, prepared as described above, was spooned into a test tube, 1.0 ml HEPES buffer was added, and the mixture was incubated at 20° C. for 10 minutes. The mixture was briefly vortexed mixed for 2 minutes, followed by 5 minutes waiting time, followed by 2 minutes vortexing, and the resulting solution added to the pressure chamber of the apparatus of FIG. 1A, which had been fitted with two stacked polycarbonate filters having a pore size of 100 nm. The solution was extruded through the filters ten times at a temperature of 20° C. The pressures employed were on the order of 200-300 psi, and the resulting flow rates were on the order of approximately 30 ml/min.

Freeze fracture micrographs of the resulting product were prepared following the procedures described above. The product was found to be a homogeneous population of substantially unilamellar liposomes having a mean diameter of approximately 70 nm as measured by freeze fracture. If desired, this mean diameter can be increased using the freeze-thaw procedures of Example 4 above.

The procedures described above were repeated using 200 nm filters, instead of 100 nm filters. In this case, pressures on the order of 100 psi were used, again resulting in flow rates of approximately 30 ml/min. Again, a homogeneous population of liposomes was produced, but in this case a substantial portion of the population was multilamellar, rather than unilamellar. The mean diameter of this population was approximately 168 nm, as measured by quasi-elastic light scattering using a Nicomp Model 200 Laser Particle Sizer (Nicomp Instruments, Inc., Santa Barbara, Calif.).

Although specific embodiments of the invention have been described and illustrated, it is to be understood that modifications can be made without departing from the invention's spirit and scope. For example, various types of apparatus other than that illustrated herein can be used to practice the present invention. In particular, because each of its steps is easily controllable, the method of the present invention is especially suited for implementation in a totally automated manner, and such implementation is specifically included within the scope of the invention. Similarly, the invention can be practiced with a variety of membrane forming materials and encapsulatable solutes other than those illustrated in the examples, and again the scope of the invention is intended to cover these variations.

TABLE I

Physical Characteristics of Vesicles Produced by Extrusion of Various Lipid Mixtures through Filters with a Pore Size of 100 nm

| LIPID | % INTEN-SITY* | MEAN DIAMETER ± S.D. (nm) | MEAN TRAPPED VOLUME** ± S.D. (ul/umole) |
|---|---|---|---|
| EPC | 48 | 71 ± 24 | 1.1 ± 0.1 (64) |
| SPC | 48 | 70 ± 23 | 1.2 ± 0.2 (13) |
| EPC/EPS (2:1) | 46 | 73 ± 25 | 1.5 (2) |
| SPC/SPS (2:1) | ND | 73 ± 20 | 2.4 (2) |
| SPE/SPS (2:1) | ND | 79 ± 36 | 2.0 (2) |
| SPS | ND | ND | 2.3 (2) |
| EPS | ND | ND | 2.2 (2) |
| EPC (Freeze-thaw) | 51 | 77 ± 16 | 2.2 ± 0.5 (17) |
| SPC (Freeze-thaw) | 48 | 94 ± 26 | 2.2 ± 0.1 (12) |
| EPC (Octylglucoside) | 49 | ND | 1.2 ± 0.1 (3) |
| EPC (REV) | 50 | ND | 1.2 (2) |

*Intensity of $^{31}$P-NMR signal remaining in the presence of 5 mM $Mn^{2+}$
**ul/umole phospholipid (number of experiments in parenthesis)

What is claimed is:

1. A method for reducing the lamellarity of a population of liposomes comprising repeatedly passing the liposomes under pressure through a filter which has a pore size (equal to or less than) no larger than about 100 nm.

2. The method of claim 1 wherein the population of liposomes is passed through the filter more than two times.

3. The method of claim 1 wherein the population of liposomes is passed through the filter at a pressure greater than 100 pounds per square inch.

4. The method of claim 3 wherein the flow rate through the filter is greater than or equal to about 20 milliliters per minute.

5. The method of claim 1 wherein the filter has straight through channels.

6. The method of claim 5 wherein the filter is a polycarbonate filter.

7. The method of claim 6 wherein the filter comprises two or more polycarbonate filters arranged in series.

8. The method of claim 1 wherein the population of liposomes has a lipid concentration greater than 60 umol/ml.

9. The method of claim 1 wherein the population of liposomes is passed through the filter more than two times at a pressure greater than 100 pounds per square inch and wherein the filter has straight through channels.

10. A method for preparing a population of substantially unilamellar liposomes comprising the steps of:
    (a) preparing multilamellar liposomes; and
    (b) repeatedly passing the liposomes under pressure through a filter which has a pore size no larger than about 100 nm.

11. The method of claim 10 wherein the liposomes are passed through the filter more than two times.

12. The method of claim 10 wherein the liposomes are passed through the filter at a pressure greater than 100 pounds per square inch.

13. The method of claim 10 wherein the flow rate through the filter is greater than or equal to about 20 milliliters per minute.

14. The method of claim 10 wherein the filter has straight through channels.

15. The method of claim 14 wherein the filter is a polycarbonate filter.

16. The method of claim 15 wherein the filter comprises two or more polycarbonate filters arranged in series.

17. The method of claim 10 wherein the population of liposomes has a lipid concentration greater than 60 umol/ml.

18. The method of claim 10 wherein the multilamellar liposomes are prepared by mechanical agitation of an aqueous suspension of one or more lipids.

19. The method of claim 10 including the additional step of subjecting the liposomes to a freeze-thaw cycle to increase their trapped volumes.

20. The method of claim 10 wherein the multilamellar liposomes are prepared by mechanical agitation of an aqueous suspension of one or more lipids, wherein the liposomes are passed through the filter more than two times at a pressure greater than 100 pounds per square inch, and wherein the filter has straight through channels.

21. The method of claim 20 including the additional step of subjecting the liposomes to a freeze-thaw cycle to increase their trapped volumes.

22. A method for preparing liposomes without the use of solvents, detergents or other extraneous materials comprising the steps of:
    (a) preparing a mixture of a lipid powder or pellet and an aqueous buffer; and
    (b) repeatedly passing the mixture under pressure through a filter, wherein the filter has a pore size less than or equal to about 100 nm, the mixture is passed through the filter more than two times, and the resulting liposomes are substantially unilamellar.

23. The method of claim 22 wherein the mixture is passed through the filter at a pressure greater than 100 pounds per square inch.

24. The method of claim 23 wherein the flow rate through the filter is greater than or equal to about 20 milliliters per minute.

25. The method of claim 23 wherein the filter has straight through channels.

26. The method of claim 25 wherein the filter is a polycarbonate filter.

27. The method of claim 26 wherein the filter comprises two or more polycarbonate filters arranged in series.

28. The method of claim 22 wherein the mixture has a lipid concentration greater than 60 umol/ml.

29. The method of claim 22 including the additional step of subjecting the liposomes to a freeze-thaw cycle to increase their trapped volumes.

* * * * *